(12) United States Patent
Ash et al.

(10) Patent No.: US 8,703,828 B2
(45) Date of Patent: *Apr. 22, 2014

(54) ANTIMICROBIAL COMPOSITIONS AND METHODS OF USE

(71) Applicant: Zurex Pharma, Inc., Middleton, WI (US)

(72) Inventors: Stephen R. Ash, Lafayette, IN (US); Janusz Steczko, West Lafayette, IN (US)

(73) Assignee: Zurex Pharma, Inc., Middleton, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/784,639

(22) Filed: Mar. 4, 2013

(65) Prior Publication Data

US 2013/0184267 A1 Jul. 18, 2013

Related U.S. Application Data

(62) Division of application No. 12/154,557, filed on May 23, 2008, now Pat. No. 8,389,583.

(51) Int. Cl.
*A61K 31/045* (2006.01)
*A61K 31/19* (2006.01)
*A61K 31/54* (2006.01)
*A01N 25/00* (2006.01)

(52) U.S. Cl.
USPC ......... 514/724; 514/574; 514/227.5; 424/405

(58) Field of Classification Search
None
See application file for complete search history.

(56) References Cited

U.S. PATENT DOCUMENTS

| | | | |
|---|---|---|---|
| 4,225,254 A | 9/1980 | Holberg et al. |
| 4,364,929 A | 12/1982 | Sasmor et al. |
| 4,677,143 A | 6/1987 | Laurin et al. |
| 5,043,357 A | 8/1991 | Hoffler et al. |
| 5,436,007 A | 7/1995 | Hartung et al. |
| 5,571,666 A | 11/1996 | Floyd et al. |
| 5,688,516 A | 11/1997 | Raad et al. |
| 5,709,672 A | 1/1998 | Illner |
| 5,811,471 A | 9/1998 | Shanbrom |
| 5,858,641 A | 1/1999 | Shanbrom |
| 5,902,283 A | 5/1999 | Darouiche et al. |
| 6,022,551 A | 2/2000 | Jampani et al. |
| 6,025,312 A | 2/2000 | Saito et al. |
| 6,034,133 A | 3/2000 | Hendley et al. |
| 6,080,417 A | 6/2000 | Kramer et al. |
| 6,166,007 A | 12/2000 | Sodermann |
| 6,183,764 B1 | 2/2001 | Shanbrom |
| 6,239,048 B1 | 5/2001 | Wilson et al. |
| 6,258,797 B1 | 7/2001 | Lehner |
| 6,346,529 B1 | 2/2002 | Floyd et al. |
| 6,350,251 B1 | 2/2002 | Prosl et al. |
| 6,361,786 B1 | 3/2002 | Shanbrom |
| 6,423,329 B1 | 7/2002 | Sine et al. |
| 6,423,706 B2 | 7/2002 | Sodermann |
| 6,447,757 B1 | 9/2002 | Orlowski et al. |
| 6,451,003 B1 | 9/2002 | Prosl et al. |
| 6,488,665 B1 | 12/2002 | Severin et al. |
| 6,592,564 B2 | 7/2003 | Finch et al. |
| 6,679,870 B1 | 1/2004 | Finch et al. |
| 6,685,694 B2 | 2/2004 | Wang et al. |
| 6,958,049 B1 | 10/2005 | Ash |
| 6,962,714 B2 | 11/2005 | Hei et al. |
| 7,422,388 B2 | 9/2008 | Tuffs et al. |
| 7,749,529 B2 | 7/2010 | Ash et al. |
| 2002/0165278 A1 | 11/2002 | Konowalchuk et al. |
| 2002/0182265 A1 | 12/2002 | Burrell et al. |
| 2003/0078242 A1 | 4/2003 | Raad et al. |
| 2003/0212443 A1 | 11/2003 | LaMuraglia |
| 2004/0092890 A1 | 5/2004 | Ash |
| 2004/0219179 A1 | 11/2004 | McDaniel |
| 2004/0225265 A1 | 11/2004 | Tapadiya |
| 2005/0013836 A1 | 1/2005 | Raad |
| 2005/0084471 A1 | 4/2005 | Andrews et al. |
| 2005/0131356 A1 | 6/2005 | Ash et al. |
| 2005/0197634 A1 | 9/2005 | Raad et al. |
| 2006/0177477 A1 | 8/2006 | Ash et al. |
| 2006/0204466 A1 | 9/2006 | Littau et al. |
| 2006/0204467 A1 | 9/2006 | Littau et al. |
| 2006/0264423 A1 | 11/2006 | Wood et al. |
| 2007/0012713 A1 | 1/2007 | Wentworth et al. |

(Continued)

FOREIGN PATENT DOCUMENTS

| | | |
|---|---|---|
| CN | 101023909 | 8/2007 |
| FR | 2 783 714 | 9/1998 |
| WO | WO 00/01391 | 1/2000 |
| WO | WO 2007/044032 | 4/2007 |
| WO | WO 2007/095576 | 8/2007 |
| WO | WO 2008/019083 | 2/2008 |

OTHER PUBLICATIONS

Extended European Search Report for 09750991.3, Apr. 3, 2013 (9 pages).

(Continued)

*Primary Examiner* — Bong-Sook Baek
(74) *Attorney, Agent, or Firm* — Leydig, Voit & Mayer, Ltd.

(57) ABSTRACT

In one aspect, compositions provide antimicrobial therapy as topical disinfectants. Particularly, one aspect relates to an alcohol containing antimicrobial composition that includes at least one paraben, a redox compound and an organic acid at a concentration of from about 1.5 percent to about 10 percent by weight, based on the total weight of the composition. In other aspects, antimicrobial compositions are used to topically sanitize wounds, skin areas and/or to disinfect surgical instruments or other surfaces. Still, in further aspects, methods, devices and kits relating to an antimicrobial composition are provided.

12 Claims, 7 Drawing Sheets

(56) References Cited

U.S. PATENT DOCUMENTS

| | | | |
|---|---|---|---|
| 2007/0105848 A1 | 5/2007 | Wood et al. |
| 2007/0112062 A1 | 5/2007 | Luengo et al. |
| 2007/0184016 A1 | 8/2007 | Macinga et al. |
| 2007/0225662 A1 | 9/2007 | Rucinski |
| 2007/0231051 A1 | 10/2007 | Flores et al. |
| 2007/0241306 A1 | 10/2007 | Wehner et al. |
| 2008/0050448 A1 | 2/2008 | Wilson et al. |
| 2008/0279907 A1 | 11/2008 | Ash et al. |

OTHER PUBLICATIONS

Chinese Search Report for 200980128718.6, Apr. 10, 2013 (1 page).

Mirja Reichel, *Alcohols for Skin Antisepsis at Clinically Relevant Skin Sites,* Antimicrobial Agents and Chemotherapy, Nov. 2009, 4778-4782, 53-11, doi:10.1128/AAC.00582-09.

ML Rotter, *Surgical hand disinfection with alcohols at various concentrations: parallel experiments using the new proposed European standards method,* Infect Control Hosp Epidemiol Oct. 1998, PMID: 9801287, (abstract).

Günter Kampf, *Efficacy of two ethanol-based skin antiseptics on the forehead at shorter applications times,* BMC Microbiology, Sep. 2007, 7-85, doi:10.1186/1471-2180-7-85.

Roberts, K. Value of Methylene Blue-Gentian Violet 5 Per Cent in Preoperative Skin Preparation. Annals of Surgery, vol. 89(2); Feb. 1929.

Ness, IF, Eklund, T. The effect of parabens on DNA, RNA and protein synthesis in *Escherichia coli* and *Bacillus subtilis*. Journal of Applied Bacteriology, vol. 54, pp. 237-242, 1983.

Russell, AS, Furr, JR. The effects of antiseptics, disinfectants and preservatives on smooth, rough and deep rough strains of *Salmonella typhimurium*. International Journal of Pharmaceutics, vol. 34, pp. 115-123, 1986.

Hesse A, Schreyger F., Tuschewitzki GJ, Classen A, and Bach D. Experimental Investigations on Dissolution of Incrustations on the Surface of Catheters. Urologia Internationalis 1989 Switzerland, vol. 44, No. 6, 1989, pp. 365-369.

Hesse, A., Nolde A., Limp, B., Marklein, G., and Tuschewitzki, GJ. In vitro Investigations into the Formation and Dissolution of Infection-Induced Catheter Encrustations, British Journal of Urology, vol. 70, No. 4, Oct. 1992, pp. 429-434.

Branson, PK., McCoy, RA., Phillips, BA., and Clifton, GD. Efficacy of 1.4 Percent Sodium Citrate in Maintaining Arterial Catheter Patency in Patients in a Medical ICU; Chest, vol. 103, No. 3, pp. 882-865. Mar. 1993.

Denyer, SP. Mechanisms of Action of Antibacterial Biocides. International Biodeterioration and Biodegradation, vol. 36, pp. 227-245, 1995.

Ma, Y., Marquis, RE. Irreversible paraben inhibition of glycolysis by *Streptococcus mutans* GS-5. Letters in Applied Microbiology, vol. 23, pp. 329-333, 1996.

Wainwright, M., Phoenix, DA., Marland, J. Waring, DRA., Bolton, FJ. A study of photobactericidal activity in phenothiazinium series, FEMS Immunology and Medical Microbiology, vol. 19, pp. 75-80, 1997.

Kristiansen, JE., Amaral, L. The potential management of resistant infections with non-antibiotics. Journal of Antimicrobial Chemotherapy, vol. 40, pp. 319-327, 1997.

Rice, L., Phoenix, DA., Wainwright, M., Waring, J. Effect of increasing methylation on the ability of methylene blue to cause diaphorase-catalysed oxidation of NADH. Biochemical Society Transactions, vol. 26, S319, 1998.

Kampf, R. Jarosch, Ruden, H. Limited effectiveness of chlorhexidine based hand disinfectants against methicillin-resistant *Staphylococcus aureus* (MRSA). Journal of Hospital Infection, vol. 38, pp. 297-303, 1998.

Wainwright, M. Phoenix, D.A., Gaskell, M., Marshall, B, Photobactericidal activity of methylene blue derivatives against vancomycin-resistant Enteroccus app. Journal of Antimicrobial Chemotherapy vol. 44, pp. 823-825, 1999.

Ash, SR, Mankus RA, Sutton JM, Criswell RE, Crull C, White L, Lowrey S; Concentrated Sodium Citrate (23%) as Catheter Lock Solution; ASN Program and Abstracts 32nd Annual Meeting and 1999 Renal Week, Miami Beach, FL, Nov. 1-8, 1999.

Ash SR, Mankus RA, Sutton JM, Criswell RE, Crull C, Velasquez KA, Smeltzer BD, Ing TS; Concentrated Sodium Citrate (23%) for Catheter Lock; Hemodial Int., vol. 4, pp. 22-31, 2000.

Usacheva, M.N., Teichert, M.C., Biel., M.A. Comparison of the Methylene Blue and Toluldine Blue Photobactericidal Efficacy against Gram-Positive and Gram-Negative Microorganisms. Lasers in Surgery and Medicine, vol. 29, pp. 165-173, 2001.

Doron, S, Friedman, M, Falash, M, Sasovnic, E, Zvia, H. Antibacterial effect of parabens against planktonic and biofilm *Streptococcus sobrinus*. International Journal of Antimicrobial Agents, vol. 18 pp. 575-578, 2001.

Shah, CB, Mittelman MW, Costerton JW, Parenteau S, Pelak M, Arsenault R, Mermel LA; Antimicrobial Activity of a Novel Catheter Lock Solution; Antimicrobial Agents and Chemotherapy, Jun. 2002, p. 1674-1679; vol. 46, No. 6, American Society for Microbiology, 2002.

Wainwright M, Crossley, KB, Methylene Blue—a Therapeutic Dye for All Seasons? Journal of Chemotherapy, vol. 14(5), pp. 431-443, Oct. 2002.

Hibbard, J. Mulberry, G, Brady, A. A Clinical Study Comparing the Skin Antisepsis and Safety of ChloraPrep, 70% Isopropyl Alchohol, and 2% Aqueous Chlorhexidine. Journal of Infusion Nursing. vol. 25, No. 4, pp. 224-249, Jul./Aug. 2002.

Usacheva, MN, Teichert, MC, Biel MA. The Interaction of Lipopolysaccharides with Phenothiazine Dyes. Lasers in Surgery and Medicine, vol. 33, pp. 311-319, 2003.

Bell AL, Gu X, Burczynski, FJ, Vercaigne, LM. Ethanol/Trisodium citrate for hemodialysis catheter lock. Clinical Nephrology, vol. 62, No. 5, pp. 369-373, Nov. 2004.

Bredin, J, Davin-Regli, A, Pages, J. Propyl paraben induces potassium efflux in *Escherichia coli*. Journal of Antimicrobial Chemotherapy, vol. 55, pp. 1013-1015, 2005.

Nguyen, T, Clare, B, Guo, W, Martinac, B. The effects of parabens on the mechanosensitive channels of *E. coli*. Eur Blophy Journal, vol. 34, No. 5, pp. 389-395, Jul. 2005.

Demidova, T.N., Hamblin, M.R. Photodynamic Inactivation of *Bacillus* spores, Mediated by Phenothiazinium Dyes. Applied and Environmental Microbiology, vol. 71, No. 11, pp. 6918-6925, 2005.

Adams, D, Quayum, M, Worthington, T, Lambert, P, Elliott, T. Evaluation of a 2% chlorhexidine gluconate in 70% isopropyl alcohol skin disinfectant. Journal of Hospital Infection, vol. 61, pp. 287-290, 2005.

Hibbard, J. Analyses Comparing the Antimicrobial Activity and Safety of Current Antiseptic Agents: A Review, Journal of Infusion Nursing, vol. 28, No. 3, pp. 194-207, May/Jun. 2005.

Brown, T.L., Gamon, S., Tester, P., Martin, R., Hosking, K., Bowkett, G.C., Gerostamoulos, D., Grayson, M.L. Can Alcohol-Based Hand-Rub Solutions Cause You to Lose Your Driver's License? Comparative Cutaneous Absorption of Various Alcohols. Antimicrobial Agents and Chemotherapy, Mar. 2007, pp. 1107.

Mimoz, O., Villeminey, S., Ragot, S., Dahyot-Flzelier, C., Laksiri, L., Petitpas, F., Debaene, B. Chlorhexidine-Based Antiseptic Solution vs Alcohol-Based Povidone-Iodlne for Central Venous Catheter Care. Arch Intern Med, vol. 167, No. 9, pp. 2066-2072. Oct. 22, 2007.

Edmiston, C., Seabrook, G., Johnson, C. Paulson, D, Beausoliel, C. Comparative of a new innovative 2% chlorhexidine gluconate-impregnated cloth with 4% chlorhexidine gluconate as topical antiseptic for preparation of the skin prior to surgery. AJIC major articles, vol. 35, No. 2, pp. 89-96, Mar. 2007.

Bleasdale, S., Trick, W., Gonzalea, I., Lyles, R., Hayden, M., Weinstein, R., Effectiveness of Chlorhoxidine Bathing to Reduce Catheter-Associated Bloodstream Infections in Medical Intensive Care Unit Patients. Arch Intern Med., vol. 167, No. 19, pp. 2073-2079, Oct. 22, 2007.

Onder, A., Chandar, J., Coakley, S., Francoeur, D., Abitbol, C., Zilleruelo, G. Controlling exit site infections-Does It decrease the Incidence of catheter-related bacteremia in children on chronic hemodialysis? Hemodialysis International, Jan. 22, 2009, vol. 13, pp. 11-18.

(56) References Cited

OTHER PUBLICATIONS

Shanks, RMQ, Sargent, JL, Martinez, RM, Graber ML, O'Toole, GA. Catheter lock solutions influence *staphylococcal* biofim formation on abiotic surfaces. Nephrol Dial Transplant, vol. 21, pp. 2247-2255, Apr. 20, 2006.

Lim, M. Infection Prevention for Cardiac Catheterization and Minimally Invasive Procedures. Supplement to VCM, pp. 7-9, Mar./Apr. 2008.

Elliott, T., Casey, A. Preoperative Skin Preparation for Minimally Invasive Surgery. Supplement to VDM, pp. 3-6, Mar./Apr. 2008.

Percival, S., Bowler, P. Woods, E. Assessing the effect of an antimicrobial wound dressing on biofilms. Wound Rep. Reg., vol. 16, pp, 52-57, 2008.

European Examination Report for 09750991.3, Dec. 13, 2013 (6 pages).

George et al., "Influence of Photosensitizer Solvent on the Mechanisms of Photoactivated Killing of Enterococcus Faecalis", *Photochemistry and Photobiology*, 84: 734-740 (2008).

ANTIMICROBIAL COMPOSITIONS AND METHODS OF USE

CROSS-REFERENCE TO RELATED APPLICATION

This application is a divisional of U.S. patent application Ser. No. 12/154,557, filed May 23, 2008, which is hereby incorporated by reference in its entirety.

The present application relates to antimicrobial compositions operable for use as preoperative scrubs and other skin disinfecting purposes, for wound care applications and as a disinfectant for sterilizing surgical instruments. More particularly, the application relates to antimicrobial compositions that are effective to achieve a rapid kill of microorganisms present on a skin surface or other surface, and that exhibit an antimicrobial effect that is persistent for an extended period of time after application.

By way of background, it is often desirable to eliminate or reduce the presence of microorganisms in an attempt to prevent infection and the spread of the microorganisms. As an example, in order to reduce the incidence of post-operative patient infection at a surgical site or at a catheter implantation site, the surrounding skin is scrubbed before surgery, or before insertion of a needle or a catheter, to eliminate or reduce the presence of microorganisms that can cause infection. Additionally, medical personnel participating in the surgical procedure must be properly disinfected. In the case of medical personnel, standard surgical procedures require disinfection of skin surfaces of the surgeon and the operating staff prior to surgery. Effective preoperative cleansing of skin is critical to reducing the risk of infection to the patient.

Another manner of reducing the incidence of surgical site infection during a surgical procedure is to ensure that the surgical instrumentation used in the surgery does not become infected. This can be accomplished, for example, by submerging surgical instruments in a disinfecting fluid bath before they are contacted with tissues of a patient during surgery. Alternatively, in the case of an instrument that is to be used multiple time during a surgery, such an instrument can be submerged in a disinfecting fluid bath between uses.

In addition to preparation for surgery, it is often necessary to disinfect or sanitize the skin surrounding an external wound or sore of a human being. In addition to having antimicrobial effect, disinfecting products for the cleansing of a wound or sore must also be formulated such that they do not harm the damaged tissue of the wound or sore.

Formulations used to disinfect skin surfaces, wounds, sores and surgical instruments desirably include antimicrobial compositions that are fast acting. An example of a fast-acting composition is a lower alcohol, such as, for example, ethanol or isopropyl alcohol. Moreover, particularly with regard to formulations used to disinfect skin surfaces, wounds and sores, such formulations desirably exhibit persistency over an extended period of time. Lower alcohols evaporate quickly, and do not have sufficient antimicrobial effect on skin surfaces to exhibit a high degree of persistency. For this reason and others, lower alcohols themselves are not sufficiently effective for preoperative scrubbing applications or other applications requiring a higher level of persistency.

The United States Food and Drug Administration (FDA) has developed performance standards for new antiseptic compositions proposed for use as a preoperative scrub or a surgical hand scrub. These performance standards require a formulation to be used as a preoperative scrub or a surgical hand scrub to be broad spectrum, fast acting, and persistent. The term "broad spectrum" is defined in this instance as having antimicrobial activity against a variety of gram positive and gram negative bacteria, and yeasts. In 1994, the FDA set forth testing procedures by which new antiseptics are tested. Requirements for patient preoperative skin preparation are outlined in the FDA Tentative Final Monograph for Healthcare Antiseptic Drug Products (Federal Register 59 [116], Jun. 17, 1994: pp. 31402-31452). The in vivo test procedure described in the 1994 FDA Tentative Final Monograph will hereinafter be referred to as the "1994 FDA TFM" test.

The antimicrobial efficacy of surgical hand scrubs and preoperative skin preparations can also be tested by any appropriate recognized test to demonstrate adequate disinfection of resident skin flora. Examples of such tests are ASTM E 1115-02, "Standard Test Method for Evaluation of Surgical Hand Scrub Formulations" (ASTM International) and EN 12791:2005, "Chemical disinfectants and antiseptics, Surgical hand disinfection, Test method and requirement (phase 2, step 2)," (CEN-Comitee Europeen de Normalisation, Brussels, Belgium). ASTM E 1173-01 provides "Standard Test Method for Evaluation of Preoperative, Precatheterization, or Preinjection Skin Preparations."

The product to be tested according to the 1994 FDA TFM test is applied to prepared skin treatment sites at the abdominal and inguinal areas of the human subjects by swabbing the formulation on the skin, after which the skin treatment site is allowed to dry (application and drying are referred to collectively herein as a "treatment"). The reduction of resident skin flora is measured at predetermined intervals after the treatment. Specifically, measurements of bacteria on the skin treatment site are taken immediately prior to application of the product to establish a "baseline" bacterial count, 10 minutes after treatment to measure the "initial" kill level, and 6 hours after treatment to measure persistency. The 1994 FDA TFM test requires that formulations reduce the mean number of bacteria 2 $\log_{10}$ (also referred to herein as a "2 Log kill") on an abdominal skin site within 10 minutes after treatment when compared with the baseline and the mean bacterial cell count on the treatment site must not subsequently exceed the baseline within 6 hours. In addition, the formulation must reduce the mean number of bacteria 3 $\log_{10}$ (also referred to herein as a "3 Log kill") on an inguinal skin site within 10 minutes after treatment when compared with the baseline at that site, and the mean bacterial cell count on the treatment site must not subsequently exceed the baseline within 6 hours after the treatment.

While various approaches can be employed to meet the requirements of the 1994 FDA TFM test, one difficulty that has been encountered is developing a product having sufficient bactericidal properties that are also tolerated well when contacted with human skin. For example, while reasonably good initial kill and persistency results can be achieved using a strongly acidic alcohol-based formulation (i.e., having a pH less than 3), such as, for example, a formulation that includes a high concentration of a lower alcohol together with an acid, the low pH can have a deleterious effect on the skin of the patient or the medical personnel. In addition, the low pH prevents the inclusion of additional antimicrobial ingredients that could enhance the antimicrobial function of the formulation because many antimicrobial compounds are inactivated by the strongly acidic nature of such a formulation. Other approaches use harsh oxidative halogens such as chlorine or iodine to achieve suitable persistence; however, such oxidative halogens are not well received by many patients and medical personnel. For example, a significant number of people are allergic to iodine.

Moreover, while products developed over the years following implementation of the 1994 FDA TFM test were found to satisfy the 1994 FDA TFM test, and were approved for sale as preoperative scrubs or other skin disinfecting products in the United States, the FDA in 2005 imposed a more stringent requirement for such skin treatment products (hereinafter the "2005 FDA Requirement"). Under the 2005 FDA Requirement, not only must the mean Log reduction of microbes on the skin treatment surface meet the parameters of the 1994 FDA TFM at the identified times after each treatment, but, in addition, the 2005 FDA Requirement mandates that the lower bound of the 95% confidence interval of the bacterial Log reduction must also exceed the effectiveness criteria set out in the 1994 FDA TFM (i.e., the criteria for microbe levels at 10 minutes post-treatment and 6 hours post-treatment compared to baseline counts at the abdominal and inguinal areas).

While Applicants are aware of no publicly available data revealing whether or not any skin disinfecting products currently available in U.S. commerce satisfy the 2005 FDA Requirement, there is speculation in the relevant field that few or possibly no products currently available in U.S. commerce satisfy the 2005 FDA Requirement. Whether or not this is the case, there is a need for additional contributions in this area of technology. In particular, an antimicrobial composition that is well tolerated after contact with human skin, that is fast acting, and that exhibits good persistency for an extended period of time is needed. The present application addresses this need.

SUMMARY

The present application relates to antimicrobial compositions for use as pre-operative scrubs and other skin disinfecting purposes. More particularly, but not exclusively, the application relates to an antimicrobial composition that is well tolerated on the skin, that is fast acting and that exhibits persistency over an extended period of time. The application also provides an antimicrobial composition that can be applied in a very short period of time without negating its excellent fast acting antimicrobial effect and its persistency. Antimicrobial compositions described herein are also effective for use in washing and disinfecting open wounds and sores, and for use in disinfecting surgical instrumentation and other surfaces.

In one form of the present application there is provided an alcohol containing antimicrobial composition that includes an organic acid; a paraben; and a redox compound. In one embodiment, the antimicrobial composition has a pH of from about 3 to about 7. In another embodiment, the antimicrobial composition includes an alcohol, an organic acid, a paraben, a redox compound and an organic salt. In yet another embodiment, there is provided an antimicrobial composition that includes a $C_1$ to $C_6$ alcohol at a concentration of at least about 30 percent by weight; citric acid at a concentration of from about 4 percent to about 8 percent by weight; a paraben at a concentration of up to about 0.6 percent by weight; and methylene blue at a concentration of up to about 0.2 percent by weight. In another embodiment, the antimicrobial composition has a pH of from about 3 to about 7. In still another embodiment, the composition also includes a citrate salt dissolved or dispersed therein.

In another form, the present application provides a method for making an antimicrobial composition that includes, (1) providing a solution of a $C_1$ to $C_6$ alcohol at a concentration of at least about 30 percent by weight; (2) dissolving therein an organic acid, a paraben and a redox compound to provide an antimicrobial composition exhibiting rapid antimicrobial effect and residual efficacy on a skin surface. In another embodiment, the method includes dissolving an organic salt in the solution. In another embodiment, the method includes dissolving a pH adjuster into the solution to provide a solution having a pH of from about 3 to about 8.

In another aspect of the application, there is provided a method that comprises: (1) providing an alcohol containing antimicrobial composition, the composition including an organic acid at a concentration of from about 1.5 percent to about 15 percent by weight based on the total weight of the composition; a paraben; and a redox compound; the composition having a pH of from about 3 to about 7; (2) identifying a patient with a topical presence of microorganisms; and (3) applying an effective amount of the composition to a skin surface of the patient to reduce the presence of microorganisms. In one embodiment, the composition is applied by providing an applicator comprising an absorbent material having the antimicrobial composition absorbed therein; and scrubbing the skin surface with the antimicrobial composition for up to about sixty seconds. In another embodiment, the composition is applied by scrubbing the skin surface with the antimicrobial composition for up to about thirty seconds. As used herein, the term "scrubbing" is intended to include various manners of applying the antimicrobial composition to the skin surface of the patient, including, for example, wiping, swabbing, dabbing, application by spraying and subsequently wiping, and the like.

In yet another form, the present application provides a kit for cleansing a skin surface, the kit including an antimicrobial composition as described herein and at least one applicator for applying the composition.

In still another form, the application provides an applicator configured for applying an antimicrobial composition as described herein to a skin surface. The applicator includes an absorbent material and the antimicrobial composition absorbed therein.

Further embodiments, forms, features, aspects, benefits, objects and advantages of the present application shall become apparent from the detailed description provided herewith.

DETAILED DESCRIPTION OF REPRESENTATIVE EMBODIMENTS

Figure 1:
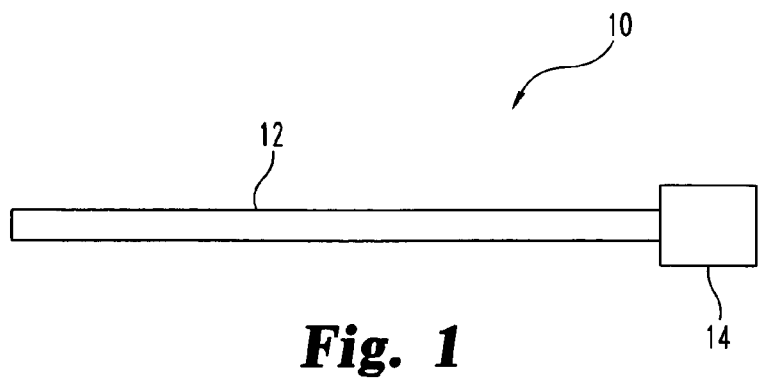
FIG. 1 is a schematic illustration of one embodiment of an applicator for applying an antimicrobial composition.

While the present invention can take many different forms, for the purpose of promoting an understanding of the principles of the invention, reference will now be made to specific embodiments and specific language will be used to describe the same. It will nevertheless be understood that no limitation of the scope of the application is thereby intended. Any alterations and further modifications of the described embodiments, and any further applications of the principles described herein are contemplated as would normally occur to one skilled in the art to which the application relates.

The present application provides compositions, methods, devices and kits useful for antimicrobial therapy. In one form, there is provided an antimicrobial composition effective for use to disinfect or sanitize an area of skin of a human being. As used herein, the term "antimicrobial composition" refers to a composition that is effective for reducing or eliminating the presence of microorganisms, including one or more of bacteria, viruses, fungi and spores. In one form, use of an antimicrobial composition in accordance with the present application yields particular advantages by providing rapid bactericidal properties combined with persistency following application of the composition. As used herein, the words "rapid bactericidal properties" are intended to refer to the ability of a composition to achieve at least a 3 Log bacterial kill at the lower bound of the 95% confidence interval on an inguinal skin surface within a period of 10 minutes after a treatment (i.e., application of the composition and drying of the skin surface), relative to the number of bacterial colony forming units (CFUs) present on the surface immediately prior to application of the composition (i.e., the "baseline") and at least a 2 Log bacterial kill at the lower bound of the 95% confidence interval on an abdominal skin surface relative to the baseline within a period of 10 minutes after a treatment. The 10 minute threshold is consistent with the FDA requirements for a preoperative scrub product. The term "persistency" refers to the ability of a composition that exhibits initial bactericidal properties to also prevent recolonization of the skin surface by bacteria to a degree that the bacterial count reaches the baseline level six hours after the treatment.

The persistency requirement of the 1994 FDA TFM test and the 2005 FDA Requirement is modest. As will be appreciated by a person of ordinary skill in the art, any time an antimicrobial formulation that rapidly kills a high percentage of microorganisms on a skin surface is applied to the skin surface, some length of time is required for any microorganisms remaining on the skin or present on adjacent skin surfaces to recolonize the skin treatment area to a level approximating that of the baseline number. Moreover, the more powerful initial kill that an antimicrobial formulation achieves, the longer the amount of time that will be required for bacteria to repopulate a skin treatment area to pre-treatment levels.

To test rapidity and magnitude of initial kill and the persistence of the kill using the 1994 FDA TFM test, the baseline number of colony forming units of a microorganism per square centimeter of a selected skin treatment area is determined ($CFU/cm^2$). Test results are obtained by determining the number of $CFU/cm^2$ of a treated skin surface at selected times after treatment of the skin surface with a test formulation. For purposes of satisfying the requirements of the 1994 FDA TFM for a pre-operative scrub, the skin surfaces to be used are in the groin (inguinal) area and in the abdominal area, and the 1994 FDA TFM requires that a pre-operative scrub exhibit a mean 3 Log kill in the groin area 10 minutes after treatment of the skin surface, a mean 2 Log kill in the abdominal area 10 minutes after treatment, and that the microorganisms do not rebound to baseline levels at either test surface 6 hours after the treatment. Under the more stringent 2005 FDA Requirement, for a new test formulation to be approved by the FDA for use as a preoperative scrub, the lower bound of the 95% confidence interval for the mean log reduction for the test product must be at least 2 logs at the abdominal site and 3 logs at the inguinal site at the 10 minutes post-treatment point, and subsequently not exceed baseline at six (6) hours. As will be appreciated by a person of ordinary skill in the art, to meet this standard, the test product must far exceed a mean 2 Log kill or 3 Log kill, respectively, at the 10 minute post-treatment point (i.e., have an extremely powerful initial kill). In addition, a product exhibiting a more thorough kill at a point 10 minutes after the treatment has a greater potential to prevent recolonization of the skin surface 6 hours after the treatment relative to a product exhibiting a less thorough kill at a point 10 minutes after the treatment.

Formulations described in the present application have been found to exhibit unexpectedly rapid and powerful initial antimicrobial effect, and a surprisingly strong persistency. Moreover, the formulations described herein are composed of ingredients that have no known adverse affects on human skin, including, for example, no known allergic reactions or irritations. With reference to one representative formulation embodiment described in the Examples below (referred to herein as the "Test Formulation"), the Test Formulation was shown to exhibit greater than a mean 3 Log kill in the abdominal skin area at 10 minutes and greater than a mean 4 Log kill in the inguinal skin area at 10 minutes post-treatment compared to the baseline CFU levels immediately prior to application of the Test Formulation. Even more astounding was that the Test Formulation exceeded the 10-minute kill requirements imposed by the 2005 FDA Requirement immediately after the treatment when the Test Formulation was applied to the skin surface after a treatment in which the product application was by swabbing for only 15 seconds in the abdominal area and 60 seconds in the inguinal area. Moreover, the mean kill level remained greater than 3 Log and 4 Log, respectively, after six hours post-treatment compared to the baseline CFU levels at the abdominal and inguinal locations. In addition, calculation of 95% confidence intervals of the data obtained following treatments of both abdominal and inguinal skin areas with the Test Formulation revealed that the lower bound of the 95% confidence intervals also exceeded the levels required by the 1994 FDA TFM.

Thus, as described in greater detail in the Examples, not only does the Test Formulation achieve an immediate kill after treatment (i.e., measured immediately after the skin treatment area is allowed to dry following application of the Test Formulation) that meets the lower bound limit imposed by the 2005 FDA Requirement, and not only do the microorganisms fail to recolonize on the treated skin surface to the original baseline levels at six hours post-treatment, but the microorganism population fails to increase by any significant amount during this six-hour period from their levels at the 10 minute post-treatment point. This is an astounding and surprising result, and provides conclusive evidence that the Test Formulation continues to impart strong antimicrobial effect against the propagation of microorganisms for at least six hours after the treatment. Moreover, the Test Formulation was found to meet and exceed the 1994 FDA TFM 10-minute requirement immediately after the scrub and meet and exceed the 6-hour requirement even when it was applied by a single pass over the skin surface being treated, thus providing for a much faster treatment process. This shows the exceptionally potent antimicrobial action of this formulation. Thus, not only does the Test Formulation significantly exceed the FDA standard at 10 minutes after treatment, but it exhibits surprisingly rapid effect and surprisingly strong persistency, even when applied quickly and in very small amounts. Moreover, this surprisingly strong antimicrobial result is achieved with a combination of ingredients that are well tolerated by the skin of patients and medical personnel. Indeed, rubbing the Test Formulation on the skin for two minutes causes no detectable redness or irritation.

In one embodiment, the antimicrobial composition includes the following main ingredients: an alcohol, an organic acid, at least one paraben and a redox compound. In addition, the composition has a pH of between about 3 and about 7. Given that the composition includes an acid, the composition can also include an ingredient that operates in the solution as a pH adjuster, if necessary to achieve a pH within the range of about 3 to about 7. In one embodiment, the pH adjuster is an organic salt. As will be set forth below, the antimicrobial composition may include ingredients in addition to the main ingredients.

In one embodiment, the alcohol exhibits rapid antimicrobial properties and facilitates the dissolution or dispersal of the other components therein. In another embodiment, the alcohol is a $C_1$ to $C_6$ alcohol. As used herein, "$C_1$," "$C_2$," "$C_3$," "$C_4$," "$C_5$" and "$C_6$" refer to alcohols having one, two, three, four, five or six carbons, respectively. The carbon arrangement of these alcohols may be branched or straight-chained. In yet another embodiment, the alcohol is a lower chain alcohol such as a $C_1$ to $C_4$ alcohol. Examples of lower chain alcohols include methanol, ethanol, propanol and butanol, as well as isomers and mixtures thereof. In a particular embodiment, the alcohol is isopropyl alcohol, which is also known as 2-propanol or isopropanol.

In one form, the concentration of alcohol in the antimicrobial composition is at least about 30 percent by weight, based on the total weight of the antimicrobial composition. For example, in one form, the antimicrobial composition includes from about 30 percent to about 85 percent, by weight, of alcohol. In a different embodiment, the concentration of alcohol in the antimicrobial composition is at least about 35 percent by weight. For example, in one form, the antimicrobial composition includes from about 35 percent to about 85 percent, by weight, of alcohol. In another embodiment, the concentration of alcohol in the antimicrobial composition is at least about 40 percent by weight. For example, in one form, the antimicrobial composition includes from about 40 percent to about 85 percent, by weight, of alcohol. In still another embodiment, the concentration of alcohol in the antimicrobial composition is at least about 45 percent by weight. For example, in one form, the antimicrobial composition includes from about 45 percent to about 75 percent, by weight, of alcohol. In yet another embodiment, the concentration of alcohol in the antimicrobial composition is at least about 50 percent by weight. For example, in one form, the antimicrobial composition includes from about 50 percent to about 75 percent, by weight, of alcohol. In another different embodiment, the concentration of alcohol in the antimicrobial composition is at least about 55 percent by weight. For example, in one form, the antimicrobial composition includes from about 55 percent to about 75 percent, by weight, of alcohol. In another embodiment, the concentration of alcohol is at least about 60 percent by weight. For example, in one form, the antimicrobial composition includes from about 60 percent to about 70 percent, by weight, of alcohol. In a further embodiment, the concentration of alcohol is at least about 65 percent by weight. In yet another embodiment, the concentration of alcohol is at least about 70 percent by weight. Still, in other alternative embodiments, the concentration of alcohol is selected from one of the following possibilities: at least about 75 percent by weight; at least about 80 percent by weight; and at least about 85 percent by weight.

The antimicrobial composition may also include alternative amounts of the alcohol. For example, in an even further embodiment, the antimicrobial composition includes from about 62 percent to about 68 percent, by weight, of alcohol. In a more particular form, the antimicrobial composition includes from about 63 percent to about 67 percent, by weight, of alcohol. Still, other variations in the amount of alcohol in the antimicrobial composition in addition to or in lieu of those set forth above are contemplated.

The organic acid included in the antimicrobial composition may vary in certain embodiments. As used herein, the term "organic acid" is used to refer to an organic compound that can dissociate to donate hydrogen and lower the pH of water below neutral (i.e., below a pH of 7). In one embodiment, the organic acid includes at least one carboxylic acid functional group. As used herein, "carboxylic acid functional group" refers to a functional group having the structural formula of COOH, which is also known as a carboxyl group. Examples of organic acids with at least one carboxylic acid functional group include carboxylic acid, formic acid, acetic acid, stearic acid, lactic acid, madelic acid, acrylic acid, oleic acid, benzoic acid, citric acid, salicylic acid, tartaric acid, succinic acid, pthalic acid, malonic acid, methacrylic acid, oxalic acid, ispcitric acid, crotonic acid, glyceric acid, p-Toluic acid, propanoic acid, heptanoic acid, butanoic acid, tartronic acid, nitroacetic acid, cyanoecetic acid, methoxyacetic acid, fluoroacetic acid, chloroacetic acid, bromoacetic acid, dichloroacetic acid, glutaric acid, trichloroacetic acid, malic acid, hexanoic acid, trimellitic acid, trimesic acid, aconitic acid, tricarballylic acid and gallic acid. In another embodiment, the organic acid includes three carboxylic acid functional groups. Examples of organic acids with three carboxylic acid groups include citric acid, isocitric acid, trimellitic acid, trimesic acid, tricarballylic acid, aconitic acid and mixtures thereof. In a particular embodiment, the organic acid is citric acid.

In one embodiment, the antimicrobial composition includes from about 1.5 percent to about 15 percent, by weight, of organic acid. In another embodiment, the antimicrobial composition includes from about 1.5 percent to about 13 percent, by weight, of organic acid. In yet another embodiment, the antimicrobial composition includes from about 1.5 percent to about 11 percent, by weight, of organic acid. In another embodiment, the antimicrobial composition includes from about 1.5 percent to about 9 percent, by weight, of organic acid. In yet another embodiment, the antimicrobial composition includes from about 1.5 percent to about 8 percent, by weight, of organic acid. In still another embodiment, the antimicrobial composition includes from about 1.5 percent to about 7 percent, by weight, of organic acid. In another embodiment, the antimicrobial composition includes from about 1.5 percent to about 6 percent, by weight, of organic acid. In a further embodiment, the antimicrobial composition includes from about 1.5 percent to about 5 percent, by weight, of organic acid. In another embodiment, the antimicrobial composition includes from about 1.5 percent to about 4 percent, by weight, of organic acid. In still other embodiments, the antimicrobial composition includes at least about 2 percent, by weight, of organic acid. In yet a further embodiment, the antimicrobial composition includes at least about 3 percent, by weight, of organic acid. In yet another embodiment, the antimicrobial composition includes at least about 4 percent, by weight, of organic acid. In a further embodiment, the antimicrobial composition includes at least about 5 percent, by weight, of organic acid. In another embodiment, the antimicrobial composition includes from about 5.5 percent to about 7.5 percent, by weight, of organic acid. In yet a further embodiment, the antimicrobial composition includes from about 6 percent to about 7 percent, by weight, of organic acid. In still another embodiment, the antimicrobial composition includes about 4.6 percent, by weight, of citric acid. Still, the subject application also contemplates different amounts of organic acid in addition to or in lieu of those set forth above.

As indicated above, the antimicrobial composition also includes at least one paraben. As used herein, the term "paraben" refers to an alkyl ester of p-hydroxybenzoic acid. Examples of paraben include methyl paraben, ethyl paraben, propyl paraben, butyl paraben and mixtures thereof. In one embodiment, the antimicrobial composition includes methyl paraben. In another embodiment, the antimicrobial composition includes propyl paraben. In still another embodiment, the antimicrobial composition includes both methyl paraben and propyl paraben. However, the use of other parabens or mixtures of parabens are also contemplated.

In one embodiment, the antimicrobial composition includes up to about 0.6 percent, by weight, of paraben(s). In another embodiment, the antimicrobial composition includes from about 0.01 percent to about 1 percent, by weight, of paraben(s). In still another embodiment, the antimicrobial composition includes from about 0.01 percent to about 0.6 percent, by weight, of paraben(s). In a further embodiment, the antimicrobial composition includes from about 0.01 percent to about 0.5 percent, by weight, of paraben(s). In another embodiment, the antimicrobial composition includes from about 0.05 percent to about 0.4 percent, by weight, of paraben(s). In still another embodiment, the antimicrobial composition includes from about 0.1 percent to about 0.35 percent, by weight, of paraben(s).

In a further, more particular embodiment, the antimicrobial composition includes up to about 0.4 percent, by weight, of methyl paraben and up to about 0.2 percent, by weight, of propyl paraben. In still another embodiment, the antimicrobial composition includes from about 0.1 percent to about 0.4 percent, by weight, of methyl paraben and from about 0.01 percent to about 0.2 percent, by weight, of propyl paraben. In yet another embodiment, the antimicrobial composition includes from about 0.15 percent to about 0.35 percent, by weight, of methyl paraben and from about 0.01 percent to about 0.2 percent, by weight, of propyl paraben. In another embodiment, the antimicrobial composition includes from about 0.2 percent to about 0.3 percent, by weight, of methyl paraben and from about 0.01 percent to about 0.2 percent, by weight, of propyl paraben. In yet a further embodiment, the antimicrobial composition includes from about 0.1 percent to about 0.4 percent, by weight, of methyl paraben and from about 0.05 percent to about 0.15 percent, by weight, of propyl paraben. In another embodiment, the antimicrobial composition includes from about 0.15 percent to about 0.35 percent, by weight, of methyl paraben and from about 0.05 percent to about 0.15 percent, by weight, of propyl paraben. In a further embodiment, the antimicrobial composition includes from about 0.2 percent to about 0.3 percent, by weight, of methyl paraben and from about 0.05 percent to about 0.15 percent, by weight, of propyl paraben.

The antimicrobial composition also includes a redox compound. For purposes of this application, the term "redox" is a shorthand term used to refer to a compound that is effective to participate in a reduction/oxidation reaction in which atoms have their oxidation number changed. "Reduction" refers to a decrease in the oxidization number of a molecule, atom or ion, or in some cases a gain of electrons, and "oxidation" refers to an increase in the oxidation number of a molecule, atom or ion, or in some cases a loss of electrons. While reduction of a molecule, atom or ion is caused in some instances by a gain of one or more electrons, and oxidation of a molecule, atom or ion is caused in some instance by a loss of one or more electrons, a change in the oxidation number does not always come as result of the transfer of electrons. In the Test Formulation described in the Examples, the redox compound is methylene blue. Without limiting the present application by any theory or mechanism by which it achieves its result, methylene blue exhibits additional chemical properties that are believed to contribute to its role in the antimicrobial composition. For example, methylene blue is a cationic compound, which is believed to cause methylene blue molecules to exhibit affinity to bacterial membranes, which are negatively charged, thereby causing methylene blue to associate with bacterial membranes, where its redox potential provides a microbial effect by altering the permeability of membranes and respiratory function of the bacteria cells. In other embodiments of the present application, the redox compound comprises a cationic redox compound. Another feature of methylene blue is that it exhibits photosensitivity, and is therefore referred to as a "photo-sensitizer." A photo-sensitizer is a chemical that readily undergoes photo excitation upon exposure to light, and is then operable to transfer its energy to other molecules in a mixture or solution, thus making the mixture or solution more sensitive to undergoing chemical reactions involved for example in the production of superoxide or singlet oxygen. While photosensitivity of the redox compound is not believed to be critical to the operation of the antimicrobial composition, a photosensitive compound provides a reservoir of energy in the antimicrobial composition, and application of light at a suitable wavelength has been observed to enhance the antimicrobial power of an antimicrobial composition that includes a photosensitive redox compound. Without being limited by any theory, it is believed that a photosensitive redox compound exhibits photoinduced electron transfer. In one embodiment of the present application, the redox compound comprises a photosensitive redox compound such as, for example, a phenothiazine dye, riboflavin or the like. In still another embodiment, the redox compound comprises a photosensitive cationic redox compound. Examples of redox compounds suitable for inclusion in the antimicrobial composition include, for example and without limitation, methylene blue, methyl methylene blue, dimethyl methylene blue, azure a, azure b, azure c, thionin, toluidine blue, methylene violet, riboflavin, brilliant crystal blue and proflavine, as well as other dyes such as, for example, rose bengal, hypericin, methylene violet, rivanol, acriflavine, trypan blue, neutral red, methylene green, acridine orange and mixtures thereof. In one embodiment, the redox compound comprises methylene blue. In yet another embodiment, the antimicrobial compositions includes a photosensitive compound in addition to the redox compound.

In one embodiment, the antimicrobial composition includes up to about 0.2 percent, by weight, of the redox compound. In still another embodiment, the antimicrobial composition includes from about 0.01 percent to about 0.2 percent, by weight, of the redox compound. In yet another embodiment, the antimicrobial composition includes from about 0.01 percent to about 0.15 percent, by weight, of the redox compound. In another embodiment, the antimicrobial composition includes from about 0.03 percent to about 0.12 percent, by weight, of the redox compound. In another embodiment, the antimicrobial composition includes from about 0.03 percent to about 0.1 percent, by weight, of the redox compound. In a further embodiment, the antimicrobial composition includes from about 0.03 percent to about 0.09 percent, by weight, of the redox compound. In another embodiment, the antimicrobial composition includes from about 0.03 percent to about 0.08 percent, by weight, of the redox compound. In a different embodiment, the antimicrobial composition includes from about 0.04 percent to about 0.07 percent, by weight, of the redox compound. In another embodiment, the antimicrobial composition includes from about 0.04 percent to about 0.06 percent, by weight, of the redox compound.

In one embodiment, the redox compound is of a type that is effective to color or stain the skin surface to which the antimicrobial composition is applied. In another embodiment, in which a photosensitive compound is present in addition to the redox compound, one or both of the photosensitive compound and the redox compound is effective to color or stain the skin surface to which the antimicrobial composition is applied. Thus, the person responsible for applying the antimicrobial composition may readily ascertain whether a particular location of the skin surface has been treated with the antimicrobial composition. Moreover, in some embodiments, the depth of the color on the skin can provide an indication of the length of time that has passed since the skin surface was treated with the antimicrobial composition.

The antimicrobial composition also optionally includes a pH adjuster, if necessary or desired to increase the pH of the composition. In one embodiment, the pH adjuster comprises a basic salt such as, for example, a basic organic salt. As used herein, the term "basic salt" refers to a compound in which the hydrogen of an acid is replaced by a metal or its equivalents, and which will raise the pH of water above neutral (i.e., above a pH of 7.0). In one embodiment, the basic salt selected for inclusion in the antimicrobial composition is an organic salt having the same organic moiety as the organic acid, thereby providing an acid/salt system based on the same organic anion. In another embodiment, the organic salt is of a different type than the organic acid. In one embodiment, the organic salt is a citrate salt. In another embodiment, the organic acid is citric acid and the organic salt is a citrate salt. Examples of citrate salt include, without limitation, sodium citrate, trisodium citrate dihydrate, sodium citrate dihydrate, potassium citrate, lithium citrate and mixtures thereof. In one specific embodiment, the citrate salt is sodium citrate. In another embodiment, the citrate salt is trisodium citrate dihydrate.

In one embodiment, the antimicrobial composition includes up to about 1 percent, by weight, of a basic organic salt. In still another embodiment, the antimicrobial composition includes from about 0.1 percent to about 0.9 percent, by weight, of a basic organic salt. In yet another embodiment, the antimicrobial composition includes from about 0.2 percent to about 0.9 percent, by weight, of a basic organic salt. In a further embodiment, the antimicrobial composition includes from about 0.2 percent to about 0.8 percent, by weight, of a basic organic salt. In another embodiment, the antimicrobial composition includes from about 0.3 percent to about 0.7 percent, by weight, of a basic organic salt. In another embodiment, the antimicrobial composition includes from about 0.4 percent to about 0.6 percent, by weight, of a basic organic salt.

It is also contemplated that the antimicrobial composition may include amounts of a basic organic salt different from those disclosed.

In one embodiment, the antimicrobial composition has a pH of from about 3 to about 8. In another embodiment, the antimicrobial composition has a pH of from about 3 to about 7. In a further form, the antimicrobial composition includes a pH of from about 3 to about 6. In yet another form, the antimicrobial composition includes a pH of from about 3 to about 5. In a different form, the antimicrobial composition includes a pH of from about 3 to about 4. As would be appreciated by those skilled in the art, it is contemplated that the pH adjuster can comprise an acidic or basic agent to adjust the pH of the antimicrobial composition.

In one embodiment of the present application, an alcohol containing antimicrobial composition includes an organic acid at a concentration in the composition of from about 1.5 percent to about 10 percent by weight based on the total weight of the composition. The antimicrobial composition has a pH of from about 3 to about 8 and also includes at least one paraben and a redox compound. In one embodiment, the antimicrobial composition includes at least about 55 percent, by weight, of isopropyl alcohol.

The antimicrobial composition may also include other pharmaceutically acceptable agents in addition to those disclosed above. By "pharmaceutically acceptable", it is meant that agents are within the scope of sound medical judgment, suitable for use in contact with tissues of humans and lower animals without undue toxicity, irritation, allergic response, and the like, and are commensurate with the reasonable benefit/risk ratio. As an example, the antimicrobial composition may include a viscosity modifying agent or thickener to change the viscosity of the composition, as would be readily ascertainable by one skilled in the art. With this type of agent, the viscosity of the composition may be changed in relation to the desired application for the composition. For example, in one form, the viscosity may be altered to provide an antimicrobial composition amenable to residing on the skin of a patient for an extended time after it is initially placed there. Such a composition could, for example, be applied to the skin at a first time and wiped from the skin at a later time when a surgical procedure is to begin, thereby increasing the ease with which the composition can be applied.

As a further example, the antimicrobial composition may include one or more of a wide variety of additives that may be incorporated to provide soothing and/or healing to the skin, to offset the drying effects of the alcohol in the solution, and/or for other reasons. For example, the composition may comprise one or more of lanolin, methyl cellulose and propylene glycol to improve the skin conditioning quality of the composition. It is understood that the term "lanolin" refers to the various forms of lanolin and its derivatives, including, for example, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin alcohols, lanolin alcohols linoleate, lanolin alcohols ricinoleate, acetate of lanolin alcohols, ricinoleate, acetate of ethoxylated alcohols-esters, hydrogenolysis of lanolin, ethoxylated hydrogenated lanolin and ethoxylated sorbitol lanolin. In another embodiment, the composition may include one or more of aloe, vitamin A, vitamin E, vitamin D, talc, calamine and kaolin. Additional ingredients that may optionally be included in the composition are fragrances, dyes, preservatives, anti-bacterial agents, anti-fungal agents and emollients. It is of course not intended that this list limit the present application, but simply provide examples of additional ingredients that might be included in the composition.

As yet another example, the antimicrobial composition may include one or more of a wide variety of additives that may be incorporated to provide pain relief and/or numbing to the skin surface contacted thereby. For example, the composition may comprise local anesthetic compounds of either the aminoamide and aminoester varieties. Examples of amino esters include, for example, Benzocaine, Chloroprocaine Cocaine, Cyclomethycaine, Dimethocaine/Larocaine, Propoxycaine, Procaine/Novocaine, Proparacaine and Tetracaine/Amethocaine. Examples of amino amides include, for example, Articaine, Bupivacaine, Carticaine, Cinchocaine/Dibucaine, Etidocaine, Levobupivacaine, Lidocaine/Lignocaine, Mepivacaine, Piperocaine, Prilocaine, Ropivacaine and Trimecaine.

While not previously discussed herein, it should be appreciated that, where applicable, the balance of the antimicrobial composition is prepared with water. Furthermore, it is contemplated that the antimicrobial composition may be provided in any suitable form, such as a gel, liquid, foam, rub or lotion, just to name a few possibilities. The antimicrobial composition may be applied to a surface or area to be disinfected in any number of ways. For example, in one embodiment, the antimicrobial composition is propelled by an aerosol or other propellant. In another embodiment, the antimicrobial composition may be sprayed with a suitable spraying device, such as a hand pump bottle sprayer.

Figure 2:
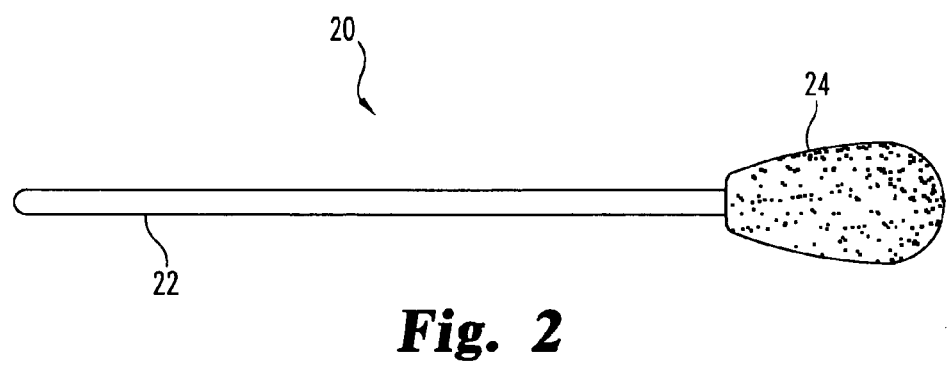
FIG. 2 is a plan view of one particular embodiment of the applicator illustrated in FIG. 1.

In another embodiment, the antimicrobial composition is first provided in an applicator and then applied to the area to be disinfected. For example, with reference to FIG. 1, an applicator 10 is schematically illustrated. Applicator 10 includes an elongated handle portion 12 with an applicator portion 14 positioned at an end thereof. Applicator portion 14 is formed of an absorbent material operable to retain a quantity of the antimicrobial composition therein to facilitate application of the antimicrobial composition to the area to be disinfected. In one form, for example, applicator portion 14 is formed from a cotton ball, rag, towel or sponge, just to name a few possibilities. In one particular applicator embodiment, shown in FIG. 2, a swab 20 includes a handle portion 22 and a cotton applicator 24 positioned at an end of handle portion 22. Cotton applicator 24 may be impregnated or saturated with the antimicrobial composition and then used to apply the antimicrobial composition to the surface or area to be disinfected.

In another variation of applicator 10, handle portion 12 houses an amount of the antimicrobial composition which is releasable therefrom to applicator portion 14. For example, in one form, the antimicrobial composition is housed in a chamber (not shown) of handle portion 12 which fluidly communicates with at least a portion of applicator portion 14 through an aperture (not shown). For example, fluid can be passed from the chamber to applicator portion 14 upon actuation of a closing member positioned between the chamber and applicator portion 14. In one non-limiting form of this example, the closing member is a relief valve which opens to release at least a portion of the antimicrobial composition to applicator portion 14 when the pressure of the antimicrobial composition in the chamber exceeds a predetermined threshold. In this form, it is contemplated that handle portion 12 is resiliently deformable and the pressure of the antimicrobial composition in the chamber generally corresponds to pressure applied to handle portion 12 by a user.

Figure 3:
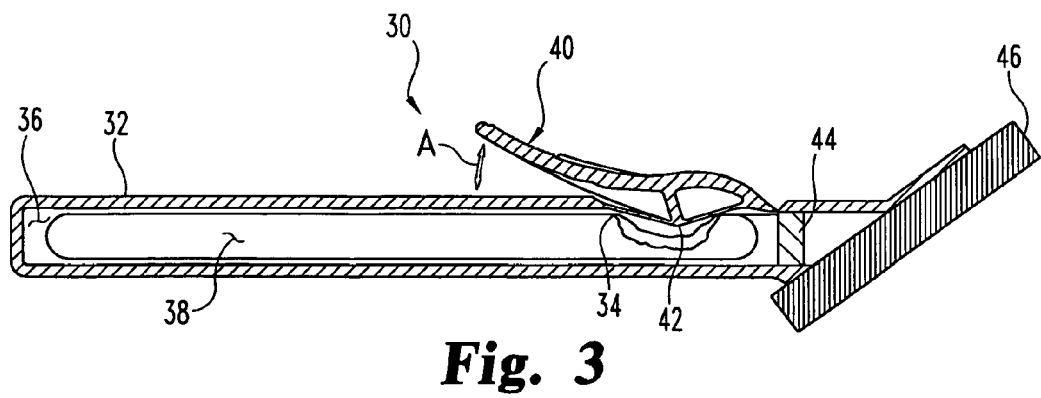
FIG. 3 is a cross-sectional side view of an alternative embodiment applicator for applying the antimicrobial composition.

Still, other types of applicators are contemplated. For example, in FIG. 3 there is shown in cross-section view an applicator 30 which includes an elongate body 32 and a porous applicator 46 positioned at an end thereof. Elongate body 32 is generally hollow and sealingly encloses an internal chamber 36 within which a container 38 filled with the antimicrobial composition is positioned. Container 38 is formed by a frangible material that breaks at a select portion where localized pressure is applied. Examples of frangible materials include glass or certain types of plastic, just to name a few possibilities. Applicator 30 also includes a lever 40 which is pivotally coupled with elongate body 32 in any suitable manner. Lever 40 is operable to apply pressure on container 38 adjacent reduced thickness body portion 34 with portion 42 of lever 40 as lever 40 is moved toward body 32, as indicated by arrow A, until container 38 breaks, as illustrated in FIG. 3. When container 38 breaks, the antimicrobial composition is released into internal chamber 36 and flows into contact with porous applicator 46 until it becomes saturated with the antimicrobial composition. In the illustrated embodiment, a filter member 44 is positioned in internal chamber 36 between container 38 and porous applicator 46 and is operable to collect and prevent any particles broken from container 38 from passing to porous applicator 46 with the antimicrobial composition. Filter member 44 may also be structured to regulate the flow of the antimicrobial composition from internal chamber 36 to porous applicator 46. While not illustrated, it should be appreciated that other configurations may be utilized for breaking container 38. For example, in one form, applicator 30 does not include lever 40 and the walls of body 32 are deformable upon application of a squeezing pressure thereto. When the walls of body 32 are squeezed inwardly, they apply a pressure to container 38 and break at least a portion of container 38. In still another form, lever 40 is replaced with a pair of oppositely positioned wing members which are squeezed together to break container 38. In another non-illustrated form, body 32 may include a sealable opening which facilitates access to chamber 36 for replacing an empty container 38 with another container full of the antimicrobial composition. Additionally or alternatively, it is contemplated that applicator 30 may be disposed of after a single use. Further details regarding an applicator similar to applicator 30 are provided in U.S. Patent Publication No. 2007/0248399, the contents of which are incorporated herein by reference in their entirety. In yet another embodiment, container 38 can be absent, and the antimicrobial composition can be contained in internal chamber 36 until a squeezing pressure is exerted on the walls of body 32, at which time the antimicrobial composition is passed through a valve and into contact with porous applicator 46.

Figure 4:
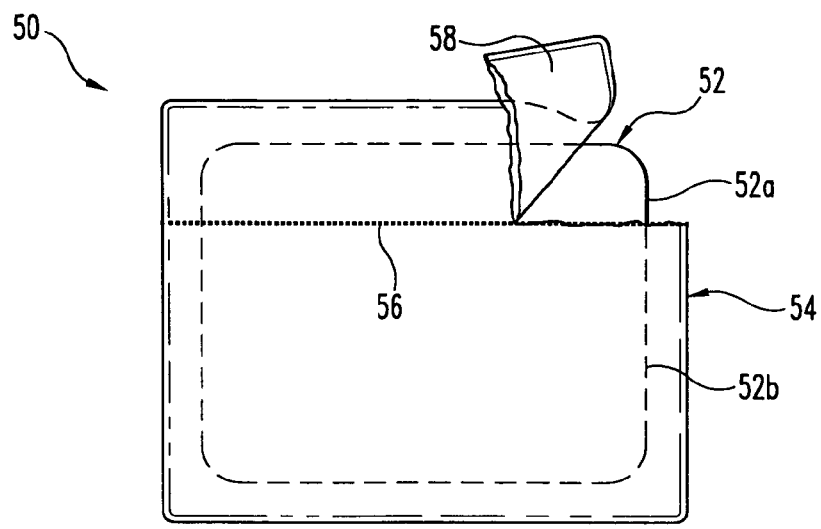
FIG. 4 is a plan view of another alternative embodiment applicator for applying the antimicrobial composition.
Figure 5:
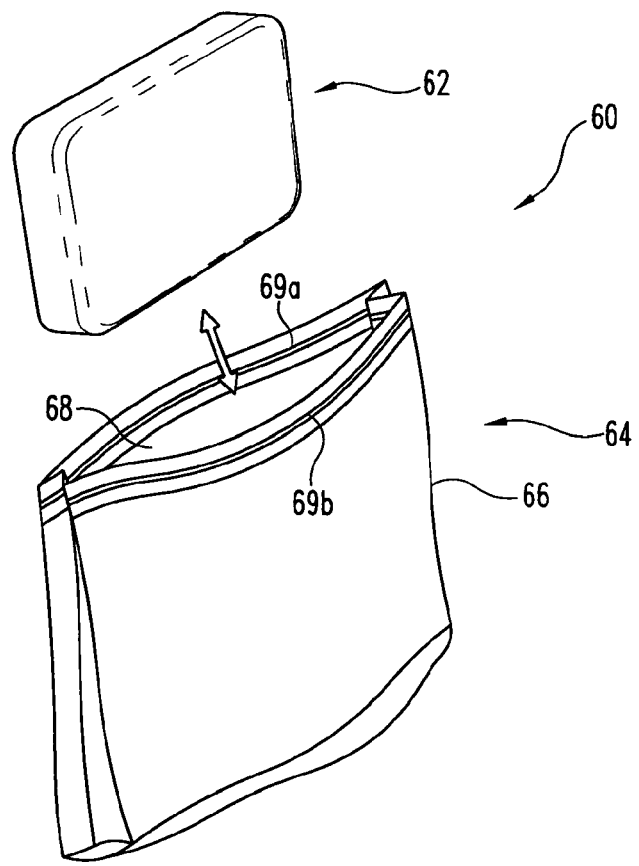
FIG. 5 is a perspective view of yet another alternative embodiment applicator for applying the antimicrobial composition.

Referring now to FIG. 4, there is shown a packaged applicator 50 that includes towelette 52. Towelette 52 is formed of an absorbent material which is saturated or impregnated with the antimicrobial composition. To prevent contamination of towelette 52, and/or evaporation of the antimicrobial composition, towelette 52 is sterilely sealed and housed in packaging 54 until use. When desired, a user may tear packaging 54 along line 56, for example, to facilitate access to towelette 52. As illustrated in FIG. 4, for example, portion 58 has been torn away from packaging 54 and portion 52a of towelette 52 has been partially exposed while portion 52b remains positioned in packaging 54. While not illustrated, it should be appreciated that package 54 can be further torn along line 56 and towelette 52 may be entirely removed from packaging 54 for use. It should also be appreciated that packaging 54 may be opened in any suitable manner which facilitates access to and removal of towelette 52 from packaging 54. Still, another applicator 60 in the form of pad 62 is shown in FIG. 5. Pad 62 is formed of an absorbent material which is saturated or impregnated with the antimicrobial composition. In one embodiment, pad 62 is formed by a gauze material. In another embodiment, pad 62 comprises a sponge. Similar to towelette 52, pad 62 may be sterilely sealed and housed in packaging 64 until use to prevent contamination and/or evaporation. In the illustrated embodiment, packaging 64 is a pouch 66 that has an interior 68 which is structured to receive pad 62. Pouch 66 includes a sealable portion 69a, 69b which remains closed until pad 62 is removed from pouch 66 for use.

It is contemplated that packaging 54 and packaging 64 may be formed of any material suitable for sterilely housing and providing access to towelette 52 and pad 62. In one particular form, packaging 54, 64 is formed of a material suitable for heating which also prevents evaporation of the antimicrobial composition during heating. In this form, packaging 54 and/or packaging 64 may be heated to a desired temperature before towelette 52 and/or pad 62 are removed for use. As a corollary, towelette 52 and/or pad 62 may be used with an increased temperature where such feature is desired. For example, when towelette 52 and/or pad 62 have been heated, they may be used to disinfect the skin of a patient while also dilating veins prior to intravascular access. As a further matter, while not illustrated, it should be appreciated that any one or more of applicators 10, 20, 30, along with applicator 70 described below, may be packaged similar to towelette 52 or pad 62.

Figure 6:
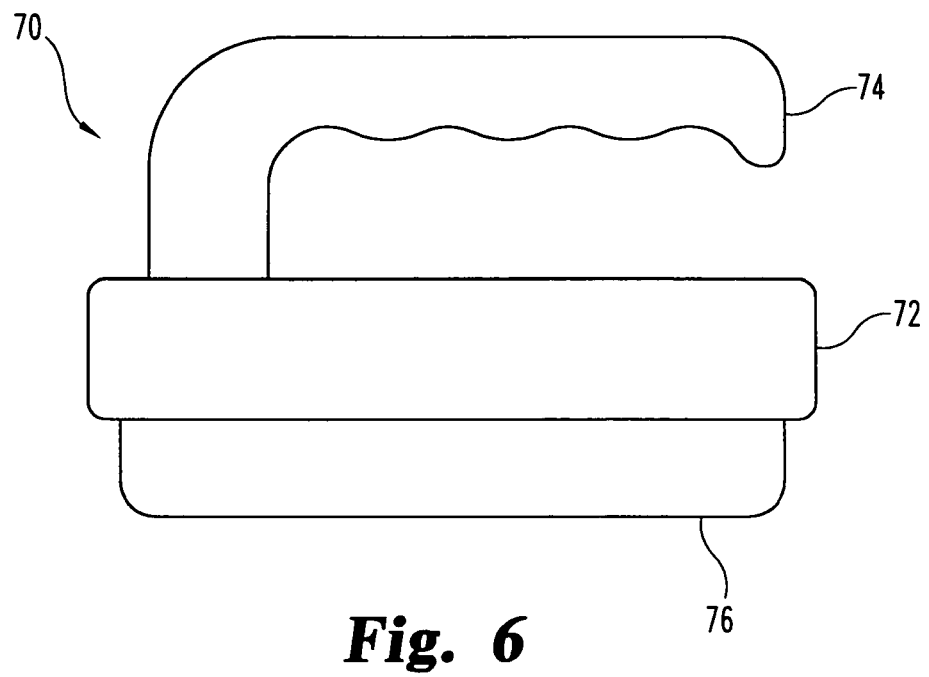
FIG. 6 is a side view of still another alternative embodiment applicator for applying the antimicrobial composition.

Another alternative embodiment applicator 70 is illustrated in FIG. 6. Applicator 70 includes a base portion 72 coupled with a handle portion 74 and a scrubbing portion 76. In one form, scrubbing portion 76 may be formed of an absorbent material, such as a sponge, which is saturated or impregnated with the antimicrobial composition. Still, in another form, scrubbing portion 76 may include a plurality of bristles. In a non-illustrated embodiment of applicator 70, base portion 72 includes a reservoir of the antimicrobial composition which is selectively releasable to scrubbing portion 76. In this embodiment, a user may apply the antimicrobial composition as needed during disinfection of a surface or area. While not previously discussed, it should be appreciated that applicators 10, 20, 30, 50, 60, 70 may be provided without the antimicrobial composition. In this form, applicators 10, 20, 30, 50, 60, 70 may be dipped into a reservoir holding the antimicrobial composition before application to a skin surface, or may be used with the antimicrobial composition applied directly to the surface or area to be disinfected.

Other types of applicators are contemplated in addition to applicators 10, 20, 30, 50, 60, 70 including, without limitation, rags, towels, cotton balls and sponges. In another embodiment, the applicator comprises a plastic container with one or more of a rag, towel, gauze, gauze pad, cotton ball, cotton swab or sponge contained therein or otherwise attached thereto. In one particular embodiment, the applicator is amenable to heating before and/or after the antimicrobial composition is applied thereto. In another embodiment, the applicator is operable to expose the antimicrobial composition to light or other form of electromagnetic radiation prior to application of the composition to a skin surface. Still, other forms contemplate supplying the applicator and the antimicrobial composition separately, and then applying the antimicrobial composition to the applicator and/or the surface or area to be disinfected.

Figure 7:
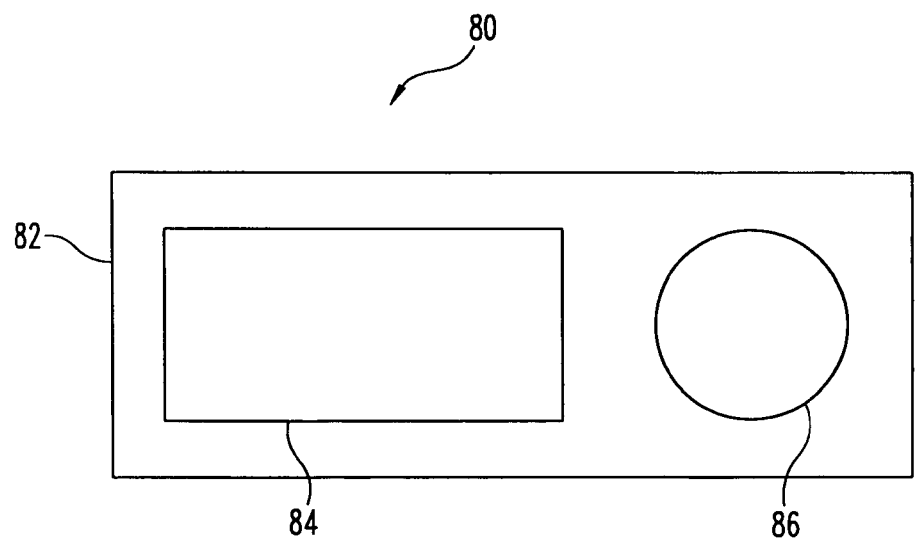
FIG. 7 is a schematic illustration of one embodiment of a kit for disinfecting.
Figure 8:
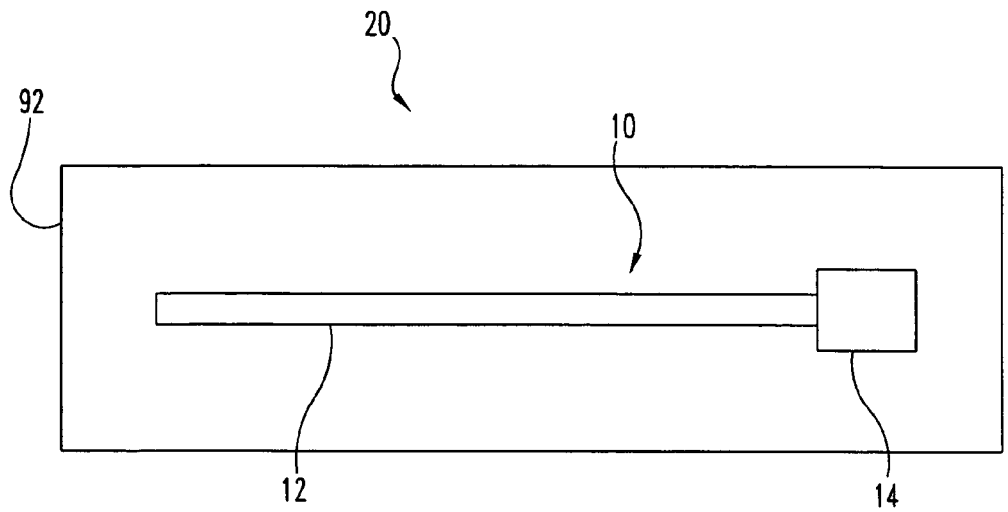
FIG. 8 is a schematic illustration of an alternative embodiment kit for disinfecting.

The present application also contemplates a kit 80, schematically illustrated in FIG. 7, for disinfecting a surface or an area, such as an area of skin of a patient. Kit 80 is generally structured for storing and transporting an applicator 84 and a container 86 that contains the antimicrobial composition. Kit 80 includes a package 82 including internal compartments (not shown) which are generally structured to hold and protect applicator 84 and container 86. It should be appreciated that package 82 can sterilely seal and house applicator 84 and container 86 until use. An alternative embodiment kit 90 for disinfecting is schematically illustrated in FIG. 8. Similar to kit 80, kit 90 is generally structured for storing and transporting applicator 10, which already includes the antimicrobial composition absorbed into applicator portion 14. Kit 90 also includes a package 92 including internal compartments (not shown) which are generally structured to hold and protect applicator 10. It should be appreciated that package 92 can sterilely seal and house applicator 10 to eliminate contamination of the antimicrobial composition at applicator portion 14 until use. While not illustrated, it should be appreciated that one or more of applicators 10, 20, 30, 50, 60, 70 may be provided in kits 80, 90. Furthermore, it is contemplated that one or both of kits 80, 90 can include one or more medical or surgical aides, instruments and devices, including, for example, but not limited to, retractors, dilators, tissue promoting cuffs, sutures, needles, syringes, scalpels, scissors, forceps, hemostats, sponges, bandages, gloves, ointments, lubricating gels, antibiotics, analgesics and instructions for use.

In another embodiment, a method includes providing an alcohol containing antimicrobial composition, identifying a patient with a topical presence of microorganisms at a location where rapid eradication of the microorganisms and persistency of microbial kill over an extended period of time is desired, and topically applying an effective amount of an antimicrobial composition to the patient to rapidly reduce the presence of microorganisms and maintain a reduced presence of microorganisms over an extended period of time. Examples of such locations include, for example, surgical sites, wound sites, skin lesions or other sores, infected surfaces, including, for example, nasal or other mucosal surfaces, and the like. The composition includes an organic acid with a concentration in the composition of from about 1.5 to about 10 percent by weight based on the total weight of the composition, at least one paraben and a redox compound.

In yet another embodiment, an antimicrobial composition includes an alcohol at a concentration of at least about 60 percent by weight; citric acid at a concentration of from about 4 percent to about 8 percent by weight; a paraben at a concentration of up to about 0.6 percent by weight; and a redox compound at a concentration of up to about 0.2 percent by weight. In another embodiment, the antimicrobial composition also includes a pH adjuster dispersed or dissolved therein. In yet another embodiment, the pH adjuster comprises an organic salt. In still another embodiment, the pH adjuster comprises citrate salt. In view of the surprisingly powerful antimicrobial effect of the Test Formulation described herein, it is believed that the concentrations of ingredients can be varied significantly without eliminating the antimicrobial effect, and such variations that do not eliminate the antimicrobial effect are expressly contemplated.

In an even further embodiment, a method includes selecting a surface or area to be disinfected or sanitized. After the surface or area has been selected, an antimicrobial composition disclosed herein is applied thereto. In one form, the area or surface is the skin of a patient and/or the skin of a medical professional. In one particular form, the area is the skin of a patient where a surgical procedure will be administered or at a site where a vascular access device is to be implanted through the patient's protective dermal layers. In another particular form, the area is the skin of a patient which has an open sore or wound. In one embodiment, the method includes applying the antimicrobial composition with a gauze pad. In one variant of this embodiment, the method includes providing a gauze pad having an antimicrobial composition absorbed therein, heating the antimicrobial composition and the gauze pad, and then scrubbing or washing skin of a patient with the gauze pad to apply the antimicrobial composition, thereby disinfecting the skin, and dilating veins prior to intravascular access. The gauze pad having an antimicrobial composition absorbed therein can be contained in a pouch prior to heating to prevent evaporation of the antimicrobial composition during heating.

In another embodiment, a method includes preoperatively scrubbing an area of a patient to be targeted during an operation with an antimicrobial composition disclosed herein. The method also includes avoiding reapplication of an antimicrobial composition at the surgical site for an extended period of time, during which time the composition exhibits persistency. In one embodiment, the extended period of time is at least about two hours. In another embodiment, the extended period of time is from about two hours to about four hours. In yet another embodiment, the extended period of time is from about four hours to about eight hours. In another embodiment, the extended period of time is from about eight hours to about twelve hours. In a further embodiment, the extended period of time is greater than about six hours. In still another embodiment, the extended period of time is greater than about ten hours. In another embodiment, the period of time is up to about 48 hours.

In still another embodiment, a kit for preparing a patient for a surgical procedure includes an antimicrobial composition disclosed herein. The kit also includes at least one applicator for applying the antimicrobial composition to a skin surface of the patient. Examples of applicators include, for example, absorbent materials suitable for having the antimicrobial composition absorbed therein. Examples include, without limitation, rags, towels, gauze, gauze pads, cotton balls, cotton swabs, and devices that include the same. The present application contemplates that the antimicrobial composition can be loaded onto the applicator immediately prior to using the application to scrub a skin surface. For example, a container of the antimicrobial composition can be sized to contain multiple doses, each of which can be dispensed from the container to an applicator in a single dose volume for use to scrub a skin treatment site. Alternatively, the antimicrobial composition can be provided in a single dose container, which can be loaded onto the applicator prior to swabbing a skin treatment area. As yet another embodiment, an antimicrobial composition can be pre-loaded onto an applicator and then packaged in a pre-loaded form. Because the antimicrobial composition includes at least one volatile ingredient, the packaging material is impermeable to the ingredients of the composition. The application also contemplates that the applicator can be configured to heat the antimicrobial composition prior to application thereof to a skin treatment site. In another embodiment, the applicator with an antimicrobial composition contained therein or absorbed thereon is positioned in a pouch and the applicator, together with the antimicrobial composition, is heated prior to application of the antimicrobial composition to a skin treatment site, for example, a catheter insertion site, where it is desirable to kill bacteria and dilate blood vessels. In one embodiment, the applicator device is configured for application of the antimicrobial composition to a surface of a person's nasal cavity. In another embodiment, the antimicrobial composition comprises a redox compound that is effective to color or stain the skin surface to which it is applied.

The present application also provides a method of inhibiting infections by sanitizing a surface, such as a surgeon's hands, a medical implant device, a medical instrument, a wound, or other surface to be sanitized. In accordance with the application, such a surface is sanitized by rinsing, soaking, swabbing or otherwise contacting a surface to be sanitized with a topical antimicrobial composition as described herein.

The following Examples are included to provide further description of the present application. It will be understood that these Examples are intended to be illustrative and not restrictive in nature.

EXAMPLE 1

An antimicrobial composition is prepared in accordance with the application to include the following concentrations in 70% isopropyl alcohol: 4.35% citric acid, 0.4% sodium citrate, 0.2% methyl paraben, 0.1% propyl paraben and 50 mg % methylene blue. The target pH of the antimicrobial composition is 3.3.

EXAMPLE 2

An antimicrobial composition is prepared in accordance with the application to include, based on the total weight of the composition, the following concentrations: 66% isopropyl alcohol, 4.9% citric acid, 0.45% sodium citrate, 0.24% methyl paraben, 0.11% propyl paraben and 0.007% methylene blue. The balance of the antimicrobial composition consists of water.

EXAMPLE 3

An antimicrobial composition is prepared in accordance with the application to include, based on the total weight of the composition, the following concentrations: 70% isopropyl alcohol, 4.6% citric acid, 0.2% methyl paraben, 0.1% propyl paraben and 0.05% methylene blue. The balance of the antimicrobial composition comprises water.

EXAMPLE 4

One liter of an antimicrobial composition was prepared by adding and mixing 43.497 g of citric acid anhydrous and 4 g sodium citrate dihydrate with 900 ml of 70% percent isopropyl alcohol. The composition was further prepared by successively adding 2 g of methyl paraben, 1 g of propyl paraben and 0.584 g of methylene blue (trihydrate). After the addition of each ingredient, the composition was thoroughly mixed. An appropriate amount of 70% isopropyl alcohol was then added to bring the total volume of the antimicrobial composition to one liter.

EXAMPLE 5

The antimicrobial composition made as described in Example 4 (referred to herein as the "Test Formulation") was studied to determine its effectiveness in vivo as a pre-operative scrub. The purpose of this study (hereinafter "Study 1") was to measure the functionality of the Test Formulation against the criteria of the Food and Drug Administration Tentative Final Monograph of Jun. 17, 1994 (FR Notice Vol. 59, No. 116) for use as a preoperative preparation (referred to herein as the "1994 FDA TFM").

The 1994 FDA TFM defines effective antimicrobial activity as a ≥2.0 $\log_{10}$ decrease in the mean number of colony-forming units (CFU) per square centimeter ($cm^2$) of abdominal skin or a ≥3.0 $\log_{10}$ decrease in the mean number of $CFU/cm^2$ of inguinal skin 10 minutes after treatment of the skin with an antiseptic product. Additionally, the mean number of $CFU/cm^2$ of skin must have remained below the baseline count for 6 hours after the treatment. The FDA has recently reevaluated these effectiveness provisions and "raised the bar" in terms of the killing effect required of a new preoperative preparation. For a test product to be considered effective under the new requirement (referred to herein as the "2005 FDA Requirement"), the lower bound of the 95% confidence interval for the mean log reduction for the test product must be at least 2 logs at the abdominal site and 3 logs at the inguinal site at the 10 minute point, and subsequently not exceed baseline at six (6) hours.

Scope of Study

The Test Formulation was applied to abdominal and inguinal sites of the subjects using a two-minute scrub at each skin treatment site, followed by drying for three minutes. Microbial samples were taken at three (3) different times relative to each treatment. For purposes of measuring time periods following a treatment, the term "treatment" is intended to refer to the entire period of time that includes applying the Test Formulation in contact with the skin surface (i.e., via a two-minute scrub in the present instance) and also the time necessary for the skin site being tested to dry (i.e., via a three-minute drying time in the present instance). Thus, a time period measured from the treatment (or "post-treatment") begins after the drying time that follows application of the Test Formulation. The three (3) different times at which microbial samples were taken relative to each scrub are set forth below:

(1) immediately prior to application of the Test Formulation (this sample is also referred to herein as the "baseline"),
(2) ten (10) minutes (+/−15 seconds) post-treatment, and
(3) six (6) hours (+/−30 minutes) post-treatment.

Testing was performed per methodology specified in the 1994 FDA TFM. Between the ten minute sampling and the six hour sampling, the inguinal and abdominal sites tested were covered with sterile gauze and semi-occlusive bandages.

Subjects

A sufficient number of overtly healthy subjects of either sex, of any race, and at least eighteen (18) years of age were admitted into the study to ensure that at least fourteen (14) post-treatment samples were obtained at each post-treatment sample time at each test site (abdominal and inguinal). All subjects free of dermatoses, cuts, lesions, or other skin disorders on or around the abdominal or inguinal (groin) test areas were eligible to participate in the study. Subjects were included if microbial counts on sampling sites were ≥2.5 $\log_{10} CFU/cm^2$ of abdominal skin and ≥4.5 $\log_{10} CFU/cm^2$ of inguinal skin. All subjects gave written informed consent before entering the trial.

Study Design

Pre-Test Period

The one (1) week (seven [7] day) period prior to product use was designated the "pre-test" period. During this time, subjects were instructed to avoid use of medicated soaps, lotions, shampoos, deodorants, etc., as well as skin contact with solvents, acids, and bases. Subjects were also instructed to avoid using tanning beds or bathing in antimicrobial treated (e.g., chlorinated) pools and/or hot tubs.

Subjects could not shave or wax anatomical sites to be treated within five (5) days prior to the Pre-Test period. The subjects were instructed not to bathe or shower during the seventy-two (72) hours period prior to their sampling times.

The baseline samples and post-treatment samples were analyzed according to a computer-generated randomization scheme.

Results

Figure 9:
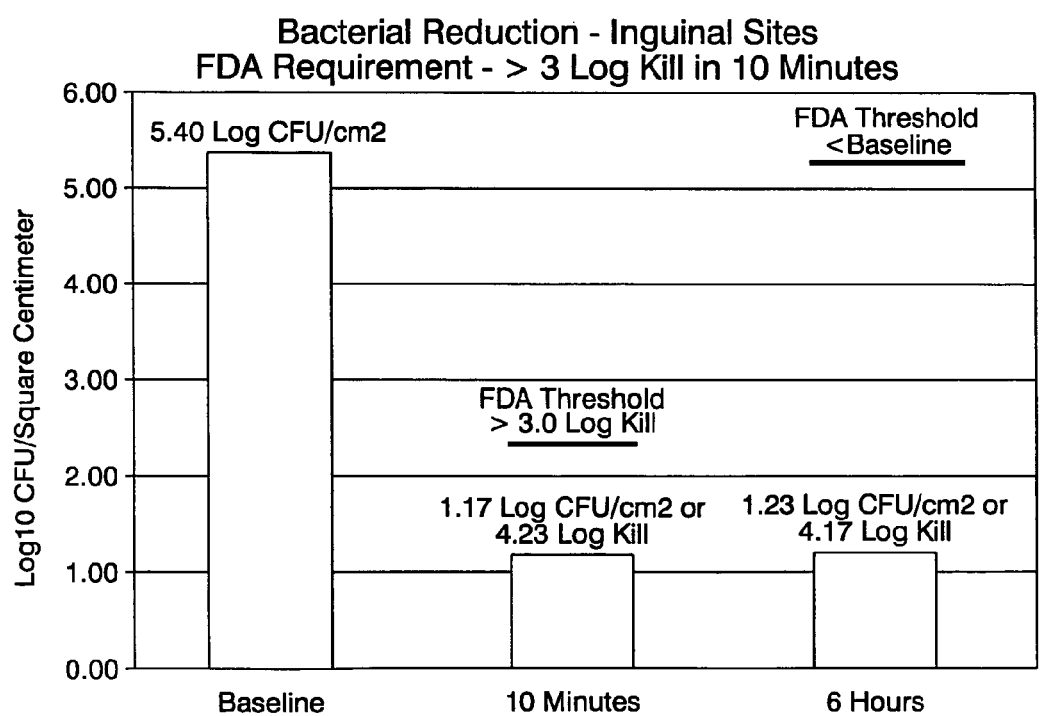
FIG. 9 is a graph depicting inguinal site test results of the bacterial reduction test described in Example 5.
Figure 10:
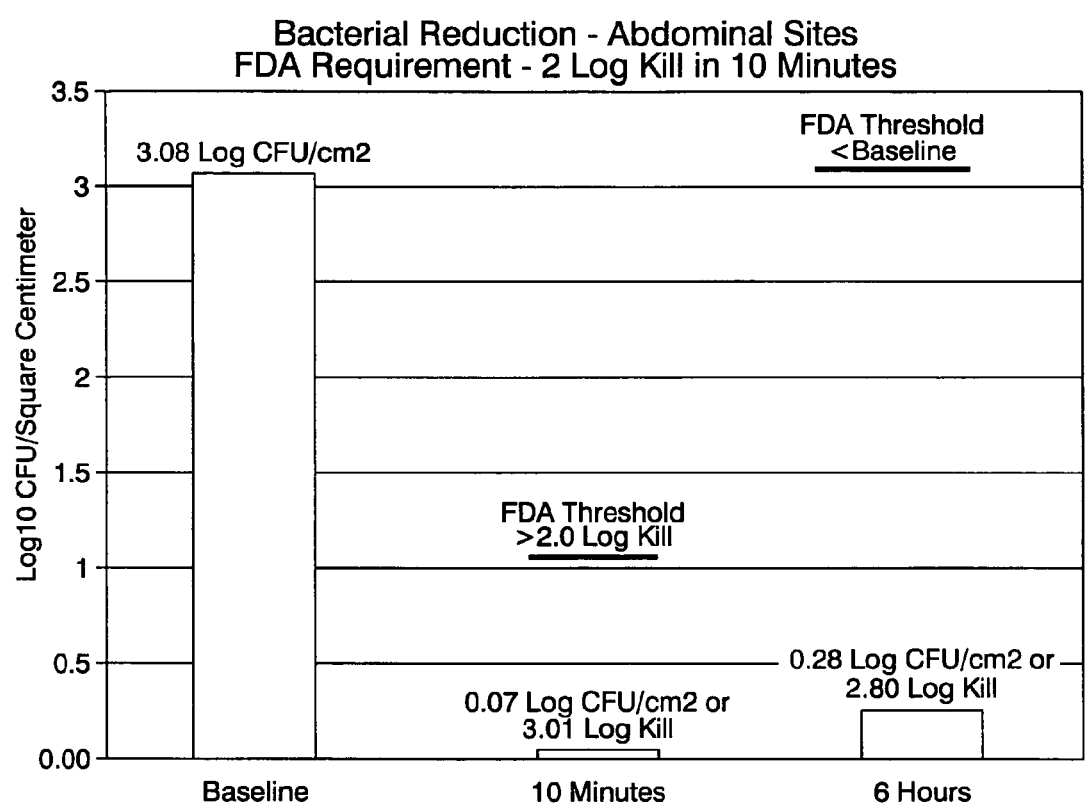
FIG. 10 is a graph depicting abdominal site test results of the bacterial reduction test described in Example 5.

The results of Test 1 are represented graphically in FIGS. 9-10 for the inguinal and abdominal treatment sites, respectively. As seen in FIGS. 9 and 10, the Test Formulation achieved mean bacterial kills at the ten minute mark that significantly exceeded the requirements set forth in the 1994 FDA TFM, and the Test Formulation exhibited excellent persistency by preventing rebound of the microbial colonies six hours after the treatment. In FIGS. 9 and 10, the levels required by the 1994 FDA TFM are identified by horizontal bars labeled "FDA Threshold." As seen in FIGS. 9 and 10, the Test Formulation exhibits a strong rapid kill and also strong persistency over at least six hours.

EXAMPLE 6

A second study (hereinafter "Study 2") was performed to (i) evaluate how quickly the Test Formulation could achieve the microbial kill levels required by the 1994 FDA TFM at the minute post-treatment point, (ii) to evaluate the lower bound of the 95% confidence interval in accordance with the 2005 FDA Requirement, and (iii) to compare different manners of applying the Test Formulation to the skin treatment surfaces. Specifically, the antimicrobial efficacy of the Test Formulation when used as a patient preoperative preparation was analyzed after treatment protocols that use three (3) different application configurations at two (2) different skin locations, i.e., on the skin of the inguinal skin site and the skin of the abdomen. Other than the items specifically mentioned below, all other test parameters and conditions were the same as described above in Example 5.

Scope of Study

The Test Formulation was applied to abdominal and inguinal sites using three (3) configurations of application at each site, as follows:

Abdominal sites:
(1) a single pass,
(2) a fifteen (15) second scrub, and
(3) a thirty (30) second scrub Inguinal sites:
(1) a thirty (30) second scrub,
(2) a sixty (60) second scrub, and
(3) a ninety (90) second scrub.

Microbial samples were taken at four (4) different times relative to each treatment. The four (4) different times at which microbial samples were taken relative to each treatment are set forth below:

(1) immediately prior to application of the Test Formulation (this sample is also referred to as the "baseline"),
(2) within thirty (30) seconds post-treatment,
(3) ten (10) minutes post-treatment, and
(4) six (6) hours post-treatment.

Testing was performed per methodology specified in the 1994 FDA TFM.

Randomization

The three (3) inguinal and three (3) abdominal test configurations were assigned randomly and bilaterally to the subjects per a computer-generated randomization schedule, such that one (1) test configuration was applied on one (1) side, and another test configuration on the opposite side of the subject at each of the two (2) test sites (inguinal and abdomen).

Results

Figure 11:
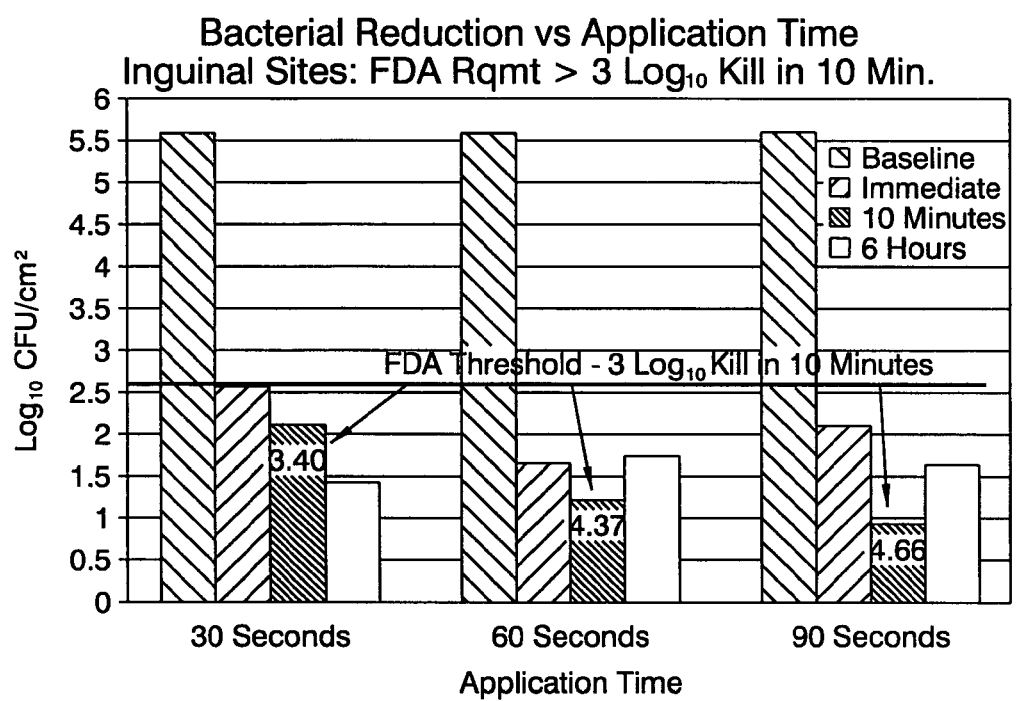
FIG. 11 is a graph depicting bacterial reduction versus application time at the inguinal site, determined as described in Example 6.
Figure 12:
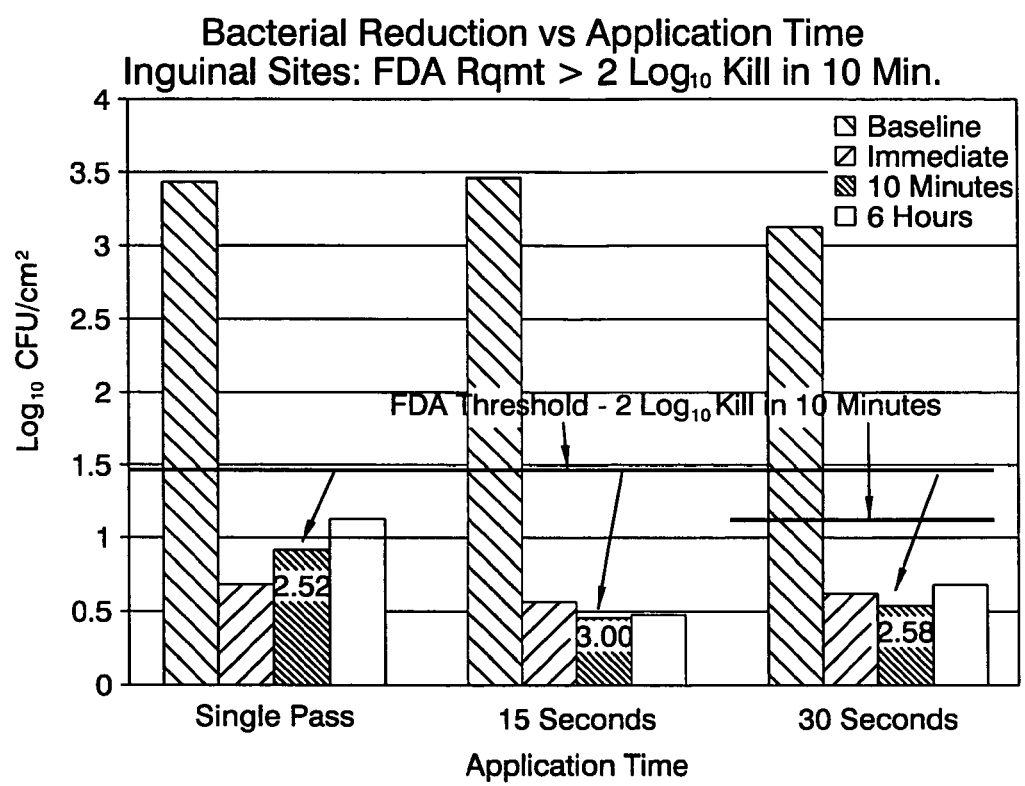
FIG. 12 is a graph depicting bacterial reduction versus application time at the abdominal site, determined as described in Example 6.

The mean Log kill results of Test 2 are represented graphically in FIGS. 11-12. As seen in FIGS. 11 and 12, the Test Formulation achieved an immediate kill (i.e., within 30 seconds post-treatment) that exceeded the 1994 FDA TFM 10-minute kill requirements, even when the Test Formulation was applied only as a 30-second scrub on the inguinal skin site (FIG. 11) and as a single pass on the abdominal skin site (FIG. 12).

The following Tables 1 and 2 set forth 95% confidence interval data for the test configurations involving 15 second application of the Test Formulation to the abdominal site and 60 second application of the Test Formulation to the inguinal site.

TABLE 1

Abdominal Site - 1994 FDA TFM Minimum $Log_{10}$ Reduction = 2.0
Application Time = 15 Seconds; Sample Size = 8

|  | Lower 95% Confidence Bound | Mean | Upper 95% Confidence Bound |
|---|---|---|---|
| Immediate | 1.97 | 2.87 | 3.77 |
| 10 Minutes | 2.41 | 3.00 | 3.58 |
| 6 Hours | 2.37 | 2.97 | 3.57 |

TABLE 2

Inguinal Site - 1994 FDA TFM Minimum $Log_{10}$ Reduction = 3.0
Application Time = 60 Seconds; Sample Size = 15

|  | Lower 95% Confidence Bound | Mean | Upper 95% Confidence Bound |
|---|---|---|---|
| Immediate | 3.06 | 3.92 | 4.79 |
| 10 Minutes | 3.56 | 4.37 | 5.19 |
| 6 Hours | 3.13 | 3.85 | 4.57 |

The 60 second and 90 second application times at the inguinal site met the 2005 FDA Requirement for a 3 Log kill at the lower bound of the 95% confidence interval immediately post-treatment (i.e., post-drying) and at 10 minutes, and the 15 second and 30 second application times at the abdominal site met the 2005 FDA Requirement for a 2 Log kill at the lower bound of the 95% confidence interval immediately post-treatment and at 10 minutes. In addition, as shown in Tables 1 and 2, the Log kill at 6 hours compared to baseline was within the 95% confidence interval of the Log kill at 10 minutes for each of the configurations set forth therein, showing that there was no significant bacterial rebound at the skin treatment sites, which far exceeds the requirements of the 1994 FDA TFM and the 2005 FDA Requirement.

The immediate kill rate by a topical antimicrobial composition is extremely important especially in the operating room where the time to surgery may be critical. The unexpected and surprising efficacy of the Test Formulation immediately following drying provides surgical flexibility and the opportunity to begin surgery more rapidly than with many other products that require a dwell time to reach maximum efficacy, generally considered to be 10 minutes post-application at moist sites, such as the groin. This, together with the near complete kill of bacteria, are astounding results that are unexpected in view of the prior art.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. An antimicrobial composition comprising (a) about 30% by weight or more of ethanol, isopropyl alcohol, n-propanol, or mixture thereof, (b) about 1.5% to 15% by weight citric acid, (c) about 0.01 percent to about 1% by weight paraben, and (d) about 0.01% to about 0.2% by weight methylene blue.

2. The composition of claim 1, wherein said composition comprises isopropyl alcohol.

3. The composition of claim 1, wherein the composition comprises methyl paraben at a concentration of from about 0.1% to about 0.4% by weight, and propyl paraben at a concentration of from about 0.01% to about 0.2% by weight.

4. The composition of claim 1, wherein the composition comprises about 0.03% to about 0.12% by weight methylene blue.

5. The composition of claim 1, wherein the composition comprises about 4% to about 8% by weight citric acid.

6. The composition of claim 1, wherein the composition comprises about 0.2% to about 0.9% by weight sodium citrate.

7. The composition of claim 1, wherein the composition comprises at least about 60% by weight isopropyl alcohol.

8. The composition of claim 1, wherein the composition comprises (a) about 30% by weight or more of ethanol, isopropyl alcohol, n-propanol, or mixture thereof, (b) about 4% to 8% by weight citric acid, (c) about 0.03% to about 0.09% by weight methylene blue, (d) about 0.1% to about 0.4% by weight methyl paraben, (e) about 0.01% to about 0.2% by weight propyl paraben, and (f) about 0.2% to about 0.9% by weight sodium citrate.

9. The composition of claim 8, wherein the composition comprises at least about 60% by weight isopropyl alcohol.

10. The composition of claim 1, wherein the composition has a pH of about 3 to about 7.

11. The antimicrobial composition of claim 1, wherein the composition is contained within an applicator comprising an absorbent material.

12. The antimicrobial composition of claim 11, wherein the applicator comprises a handle portion comprising a chamber for housing the antimicrobial composition, and an applicator portion comprising an absorbent material in fluid communication with the handle portion.

* * * * *